United States Patent
Sun et al.

(10) Patent No.: US 11,621,110 B2
(45) Date of Patent: Apr. 4, 2023

(54) ELECTROMAGNETIC DEVICE FOR MANIPULATING A MAGNETIC-RESPONSIVE ROBOTIC DEVICE

(71) Applicant: City University of Hong Kong, Kowloon (HK)

(72) Inventors: Dong Sun, Kowloon (HK); Dongfang Li, Kowloon (HK)

(73) Assignee: City University of Hong Kong, Kowloon (HK)

( * ) Notice: Subject to any disclaimer, the term of this patent is extended or adjusted under 35 U.S.C. 154(b) by 1001 days.

(21) Appl. No.: 16/406,207

(22) Filed: May 8, 2019

(65) Prior Publication Data

US 2020/0357554 A1 Nov. 12, 2020

(51) Int. Cl.
| | |
|---|---|
| *H01F 7/20* | (2006.01) |
| *H01F 27/06* | (2006.01) |
| *B25J 13/08* | (2006.01) |
| *H01F 27/28* | (2006.01) |
| *B25J 7/00* | (2006.01) |
| *H01F 27/24* | (2006.01) |

(52) U.S. Cl.
CPC ............ *H01F 7/20* (2013.01); *B25J 7/00* (2013.01); *B25J 13/087* (2013.01); *H01F 7/206* (2013.01); *H01F 27/06* (2013.01); *H01F 27/24* (2013.01); *H01F 27/2823* (2013.01)

(58) Field of Classification Search
CPC .................................... H01F 7/20; H01F 7/206
USPC ........................................ 335/219, 299, 285
See application file for complete search history.

(56) References Cited

U.S. PATENT DOCUMENTS

| | | | | |
|---|---|---|---|---|
| 3,460,083 A | * | 8/1969 | Johnson ................ | H01F 7/0284 335/297 |
| 4,153,889 A | * | 5/1979 | Ikegami ................... | H01F 7/20 335/209 |
| 4,381,490 A | * | 4/1983 | Peters ...................... | H01S 1/06 335/297 |

(Continued)

FOREIGN PATENT DOCUMENTS

| | | |
|---|---|---|
| WO | 2013168852 | 11/2013 |
| WO | 2016151595 | 9/2016 |

OTHER PUBLICATIONS

M. P. Kummer, et al, "OctoMag: An electromagnetic system for 5-DOF wireless micromanipulation", IEEE Trans. Robot., 26, 1006-1017, (2010).

(Continued)

*Primary Examiner* — Alexander Talpalatski
(74) *Attorney, Agent, or Firm* — Renner Kenner Greive Bobak Taylor & Weber

(57) ABSTRACT

An electromagnetic device for manipulating a magnetic-responsive robotic device, and an electromagnetic apparatus incorporate one or more such electromagnetic device. The electromagnetic device includes a magnetic core 200 having a first portion and a second portion extends from one side of the first portion. The first portion has a first cross section and defining a first central axis. The second portion has a second cross section smaller than the first cross section, and defines a second central axis parallel to the first central axis. A first electromagnetic coil is arranged around the first cylindrical portion. A second electromagnetic coil is arranged around the second cylindrical portion.

31 Claims, 17 Drawing Sheets

(56) References Cited

U.S. PATENT DOCUMENTS

| | | | | |
|---|---|---|---|---|
| 5,243,314 | A * | 9/1993 | Maruyama | B23Q 3/1546 |
| | | | | 269/8 |
| 5,568,109 | A * | 10/1996 | Takayama | H05H 7/04 |
| | | | | 335/297 |
| 6,229,422 | B1 * | 5/2001 | Pignataro | H01F 7/206 |
| | | | | 335/289 |
| 7,479,859 | B2 * | 1/2009 | Gerber | H01F 13/00 |
| | | | | 209/217 |
| 9,373,443 | B2 * | 6/2016 | Kim | H01F 38/14 |
| 9,759,789 | B2 * | 9/2017 | Schmale | A61B 5/0515 |
| 2004/0209281 | A1 | 10/2004 | Monajembashi | |
| 2010/0204674 | A1 | 8/2010 | Forbes et al. | |
| 2013/0060130 | A1 | 3/2013 | Park et al. | |
| 2017/0207015 | A1 * | 7/2017 | Premaratne | A61N 2/02 |
| 2018/0071505 | A1 | 3/2018 | Lo et al. | |
| 2020/0227191 | A1 * | 7/2020 | Choi | H01F 7/04 |

OTHER PUBLICATIONS

E. Diller, et al, "Six-degree-of freedom magnetic actuation for wireless microrobotics", International Journal of Roboics Research, 35, 114 128, (2015).

S. Schuerle, et al, "Three-Dimensional Magnetic Manipulation of Micro- and Nanostructures for Applications in Life Sciences", IEEE Transactions on Magnetics, 49, 321-330, (2013).

V. Garcia-Gradilla, et al, "Functionalized ultrasound-propelled magnetically guided nanomotors: Toward practical biomedical applications", ACS Nano, 7, 9232-9240, (2013).

X. Li, et al, "Design of a robust unified controller for cell manipulation with a robot-aided optical tweezers system". Automatica, 55, 279-286, (2015).

B. R. Donald, et al, "An untethered, electrostatic, globally controllable MEMS micro-robot", Journal of Microelectromechanical Systems, 15, 1-15, (2006).

* cited by examiner

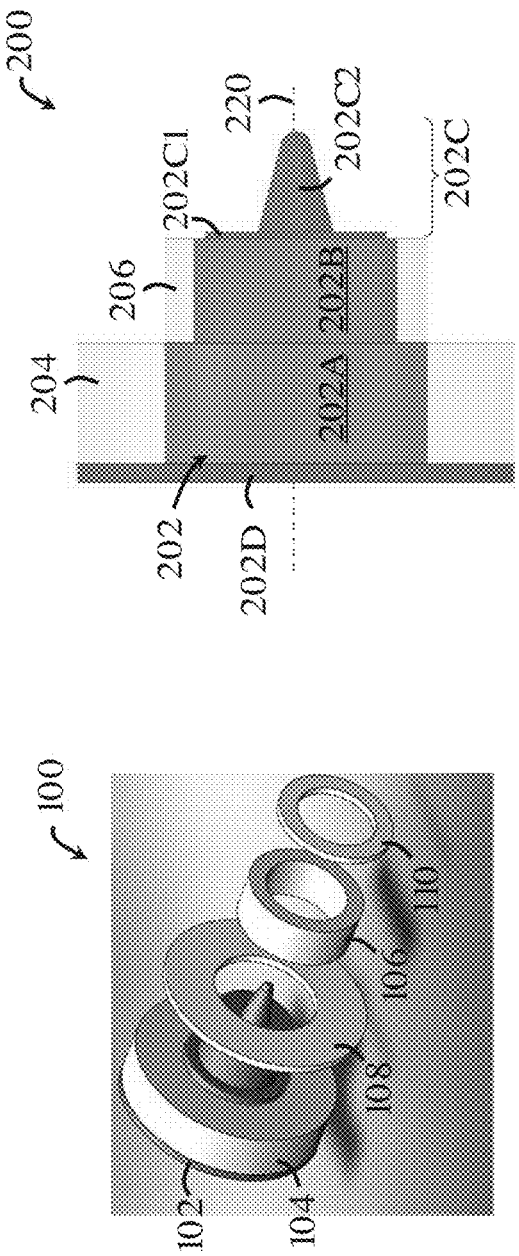
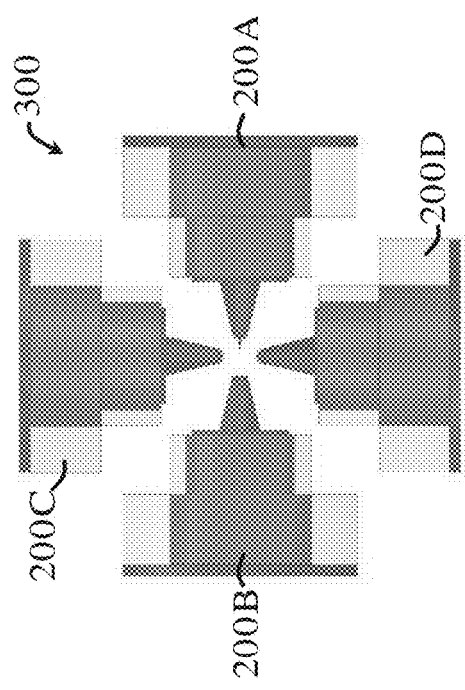

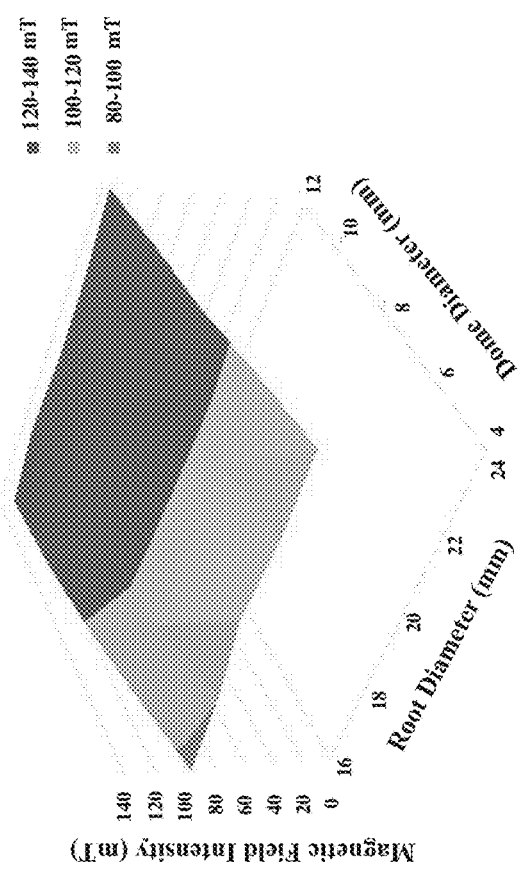
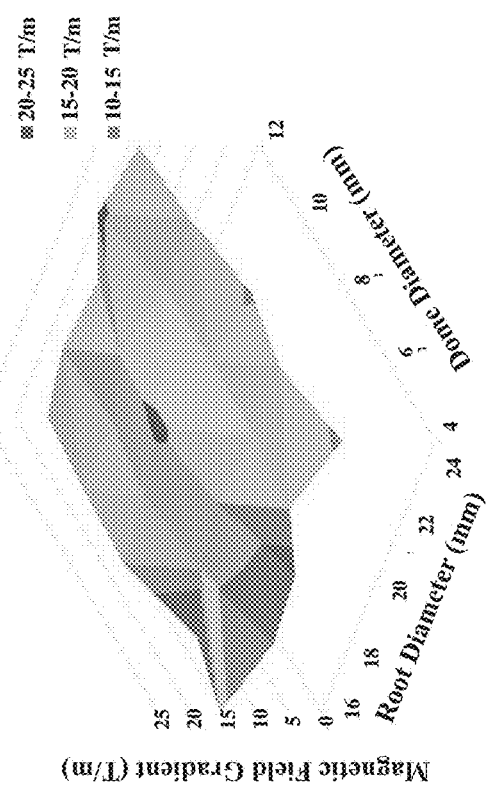
Figure 3A
Figure 3B

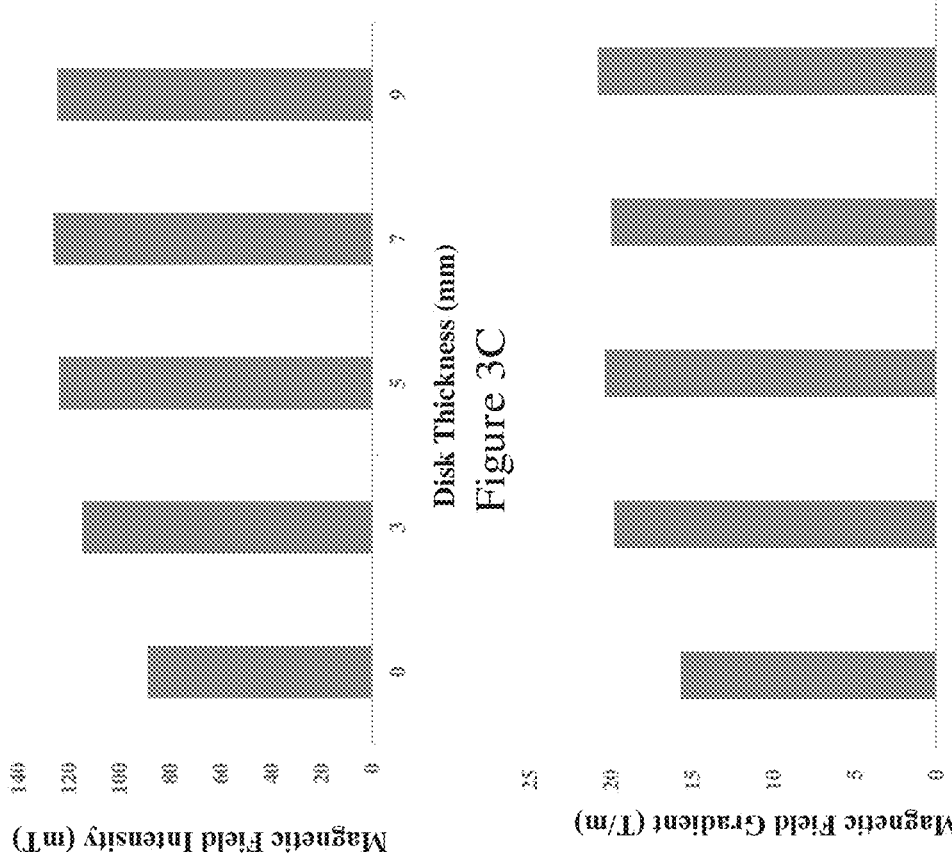

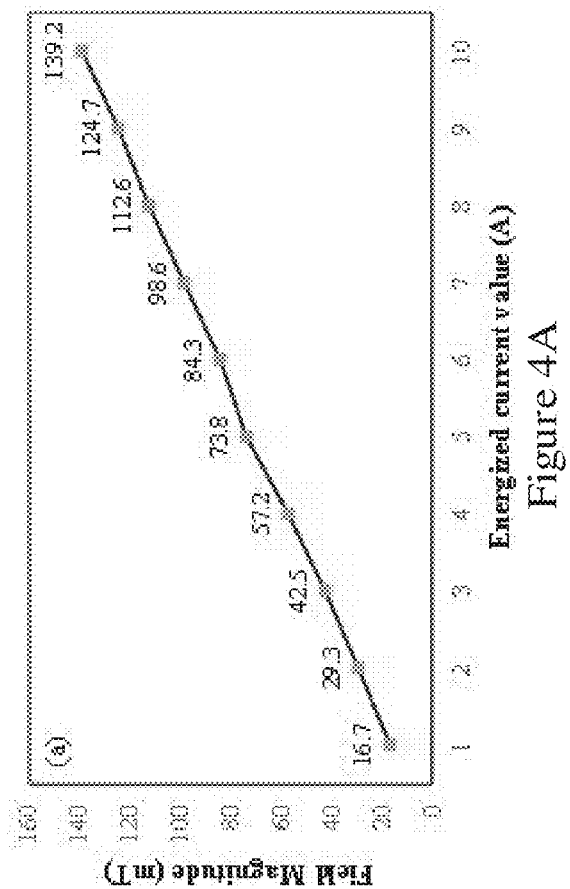
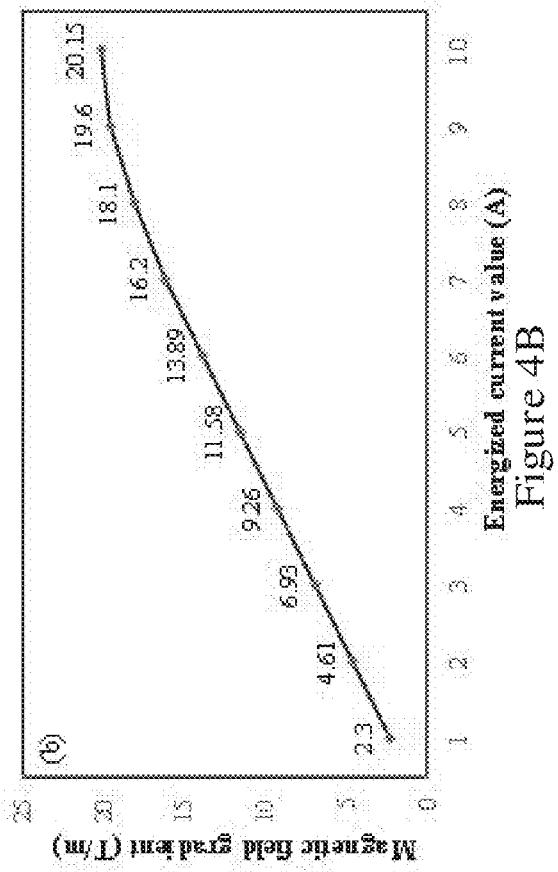
Figure 4A
Figure 4B

ELECTROMAGNETIC DEVICE FOR MANIPULATING A MAGNETIC-RESPONSIVE ROBOTIC DEVICE

TECHNICAL FIELD

The invention relates to an electromagnetic device for manipulating magnetic-responsive robotic device such as a magnetic-responsive microrobot suited for in vivo or in vitro biomedical applications.

BACKGROUND

Robotic devices are playing an increasingly important role in in the advancement of biological science. In recent biological research and applications, robotic devices are used in vivo or in vitro to carry and deliver chemicals (e.g., drugs). These robotic devices are usually passive, meaning that they do not have their own power source and is manipulated by an external movement source. The external source interacts with the robotic device optically, electrically, electromagnetically, ultrasonically, chemically, etc., to control its movement and action. Problematically, however, the in vivo and in vitro environment in which the robotic device is arranged and in which the robotic device is to be controlled can in some cases be quite viscous and harsh. This complicates the control of the robotic devices.

SUMMARY OF THE INVENTION

It is an object of the invention to address the above needs, to overcome or substantially ameliorate the above disadvantages or, more generally, to provide an improved electromagnetic device that can provide a sufficiently strong magnetic field and gradient for manipulating a magnetic-responsive robotic device. It is an object of the invention to provide a more efficient and reliable control of the magnetic-responsive robotic device, e.g., in applications involving harsh and viscous environments.

In accordance with a first aspect of the invention, there is provided an electromagnetic device for manipulating a magnetic-responsive robotic device, including: a magnetic core having a first portion and a second portion extending from one side of the first portion. The first portion has a first cross section and defines a first central axis. The second portion has a second cross section smaller than the first cross section, and defines a second central axis parallel to the first central axis. A first electromagnetic coil is arranged around the first portion. A second electromagnetic coil is arranged around the second portion.

In one embodiment of the first aspect, the second portion forms a stepped portion.

In one embodiment of the first aspect, the first central axis and second central axis are collinear.

In one embodiment of the first aspect, the first cross section has a first shape, the second cross section has a second shape, and the first shape is the same as the second shape.

In one embodiment of the first aspect, the first portion is cylindrical and/or the second portion is cylindrical.

In one embodiment of the first aspect, a ratio of a diameter of the first portion to a diameter of the second portion is between 1.1 to 1.5, and preferably about 1.3. In one example, a diameter of the first portion is about 70 mm, a diameter of the second portion is about 54 mm, and a length of the first and second portion is about 65 mm.

In one embodiment of the first aspect, the magnetic core further includes a third portion extending from one side of the second portion opposite the first portion, the third portion defining a third central axis parallel to the first and second central axes.

In one embodiment of the first aspect, the first, second, and third central axes are collinear.

In one embodiment of the first aspect, the third portion is cylindrical. In one example, the third portion has a diameter of about 8 mm and a length of about 30 mm.

In one embodiment of the first aspect, the third portion tapers from the second portion. Preferably, the third portion includes a generally conical portion or a generally pyramidal portion. The third portion may be a generally conical portion with a base and a tip, and the generally conical portion is formed by a frustoconical portion that extends from the base and a rounded tip portion at the tip. The rounded tip may be in the form of a semi-ellipsoid. The frustoconical portion may have a first end and a second end extending from the base to towards the tip. In one example, the first end has a diameter of 16 mm to 24 mm and the second end has a diameter of 4 mm to 12 mm. In one preferred embodiment, the first end has a diameter of 20 mm and the second end has a diameter of 8 mm. In another preferred embodiment, the first end has a diameter of 22 mm and the second end has a diameter of 12 mm.

In one embodiment of the first aspect, the third portion further includes a thin intermediate portion arranged between the second portion and the generally conical portion. The thin intermediate portion may be cylindrical. Preferably, a cross section of the intermediate portion is smaller than the second cross section of the second portion.

In one embodiment of the first aspect, the magnetic core further includes a fourth portion extending from the first portion opposite to the second portion. The fourth portion has a fourth cross section larger than the first cross section, and defines a fourth central axis parallel to the first and second central axes. In one embodiment of the first aspect, the first, second, and fourth central axes are collinear. In one embodiment of the first aspect, the first, second, third, and fourth central axes are collinear.

In one embodiment of the first aspect, the first cross section has a first shape, the fourth cross section with a fourth shape, and the first shape is the same as the fourth shape. In one embodiment of the first aspect, the fourth portion is cylindrical. The fourth portion may have a thickness (axial) of up to about 9 mm, up to about 7 mm, up to about 5 mm, or up to about 3 mm.

In one embodiment of the first aspect, the second electromagnetic coil includes 100 to 300 turns, more preferably 180 to 200 turns. The second electromagnetic coil may include about 190 turns. In one example, the second electromagnetic coil is formed by one or more copper wires such as one or more enameled copper wires. The one or more copper wires may have a diameter of about 1 mm.

In one embodiment of the first aspect, the first electromagnetic coil includes 300 to 900 turns, more preferably 600 to 620 turns. The first electromagnetic coil may include about 610 turns. In one example, the first electromagnetic coil is formed by one or more copper wires such as one or more enameled copper wires. The one or more copper wires may have a diameter of about 1 mm.

In one embodiment of the first aspect, the magnetic core is an iron core made of DT4E material.

In one embodiment of the first aspect, the robotic device is a microrobot for biomedical applications (e.g., drug delivery, cell transfer, etc.).

In accordance with a second aspect of the invention, there is provided an electromagnetic device for manipulating a magnetic-responsive robotic device, comprising a magnetic core having a first end and a second end, and one or more electromagnetic coils arranged around the magnetic core. The magnetic core has a cross section that generally (i.e., need not be continuously) reduces from the first end to the second end.

In one embodiment of the second aspect, the magnetic core includes a first portion with a first cross section and defining a first central axis; a second portion extending from one side of the first portion, with a second cross section and defining a second central axis; a third portion extending from one side of the second portion opposite the first portion, with a third cross section and defining a third central axis; and a fourth portion extending from the first portion opposite to the second portion, with a fourth cross section and defining a fourth central axis. The first, second, third, and fourth axes are parallel. The fourth cross section is larger than the first cross section, the first cross section is larger than the second cross section, and the second cross section is larger than the third cross section.

In one embodiment of the second aspect, the first, second, third, and fourth axes are collinear.

In one embodiment of the second aspect, the first cross section has a first shape, the second cross section has a second shape, the third cross section has a third shape, and the fourth portion has a fourth shape. The first, second, third, and fourth shape are substantially identical (but of different size).

In one embodiment of the second aspect, the one or more electromagnetic coils includes a first electromagnetic coil arranged around the first portion; and a second electromagnetic coil arranged around the second portion.

In one embodiment of the second aspect, the first, second, and fourth portions are cylindrical. The third potion may also be cylindrical. Alternatively, the third potion may be a generally conical portion with a base and a tip. The generally conical portion may be formed by a frustoconical portion that extends from the base and a rounded tip portion at the tip. The rounded tip may be in the form of a semi-ellipsoid. In one embodiment of the second aspect, the third portion further includes a thin intermediate portion arranged between the second portion and the generally conical portion. The thin intermediate portion may be cylindrical, and a cross section of the intermediate portion is smaller than a cross section of the second portion.

In accordance with a third aspect of the invention, there is provided an electromagnetic apparatus for manipulating a magnetic-responsive robotic device, comprising a plurality of electromagnetic devices of the first aspect or of the second aspect; and a mount for mounting the plurality of electromagnetic devices.

In one embodiment of the third aspect, the plurality of electromagnetic devices are angularly spaced apart.

In one embodiment of the third aspect, the plurality of electromagnetic devices are angularly spaced apart evenly. Alternatively, the plurality of electromagnetic devices may be spaced apart unevenly.

In one embodiment of the third aspect, the plurality of electromagnetic devices includes four electromagnetic devices. In one example, the four electromagnetic devices may be formed a first pair of opposed electromagnetic devices and a second pair of opposed electromagnetic devices.

In one embodiment of the third aspect, the mount supports the plurality of electromagnetic devices such that the plurality of electromagnetic devices generally lies on the same plane.

In one embodiment of the third aspect, the electromagnetic apparatus further includes a power supply arranged to be operably connected with the plurality of electromagnetic devices for selectively energizing the plurality of electromagnetic devices. The power supply may be a programmable power supply.

In one embodiment of the third aspect, the electromagnetic apparatus further includes an imaging device, operably connected with the power supply, for imaging the magnetic-responsive robotic device when the magnetic-responsive robotic device is manipulated by the electromagnetic apparatus. The imaging device may include one or more of: a camera, a microscope, etc.

In one embodiment of the third aspect, the magnetic-responsive robotic device includes magnetic-responsive materials and the electromagnetic apparatus is arranged to saturate the magnetic-responsive material of the magnetic-responsive robotic device.

In accordance with a fourth aspect of the invention, there is provided magnetic core of the first aspect.

In accordance with a fifth aspect of the invention, there is provided magnetic core of the second aspect.

BRIEF DESCRIPTION OF THE DRAWINGS

Embodiments of the invention will now be described, by way of example, with reference to the accompanying drawings in which:

FIG. 1A is an exploded view of an electromagnetic device in one embodiment of the invention;

FIG. 1B is a section view of an electromagnetic device in one embodiment of the invention;

FIG. 1C is a plan view of an electromagnetic apparatus having four electromagnetic devices of FIG. 1B;

FIG. 3A is a plot showing the simulated variation of magnetic field intensity (mT) of the electromagnetic device of FIG. 1B for different diameters (mm) of the root and of the dome of the probe section;

FIG. 3B is a plot showing the simulated variation of magnetic field gradient (T/m) of the electromagnetic device of FIG. 1B for different diameters (mm) of the root and of the dome of the probe section;

FIG. 3C is a graph showing the simulated variation of magnetic field intensity (mT) of the electromagnetic device of FIG. 1B for different thicknesses (mm) of the disk portion at the base of the probe section;

FIG. 3D is a graph showing the simulated variation of magnetic field gradient (T/m) of the electromagnetic device of FIG. 1B for different thicknesses (mm) of the disk portion at the base of the probe section;

FIG. 4A is a plot showing the simulated variation of the magnetic field intensity (mT) produced by the electromagnetic apparatus of FIG. 1C under different coil energization currents (A);

FIG. 4B is a plot showing the simulated variation of the magnetic field gradient (T/m) produced by the electromagnetic apparatus of FIG. 1C under different coil energization currents (A);

DETAILED DESCRIPTION OF THE PREFERRED EMBODIMENT

Figure 1E:
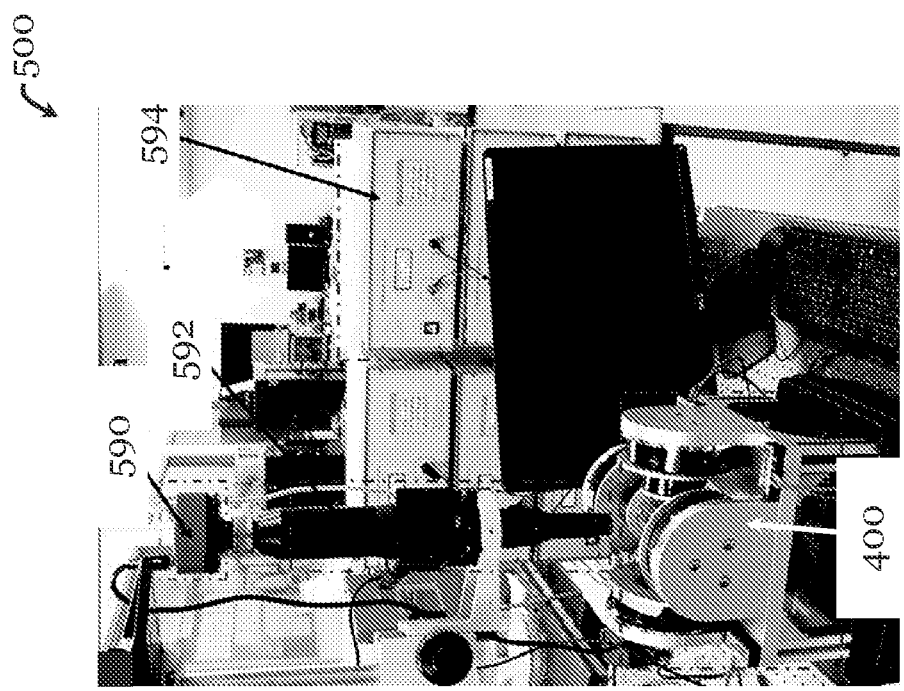
FIG. 1E is a system incorporating the electromagnetic apparatus of FIG. 1D.

FIG. 1A shows an electromagnetic device 100 for manipulating a magnetic-responsive robotic device in one embodiment of the invention. The electromagnetic device 100 includes, generally, a magnetic core 102, a larger electromagnetic coil 104 arranged around the magnetic core 102, and a smaller electromagnetic coil 106 arranged around the magnetic core 102. A first annular plate 108 is arranged at an axial end of the larger electromagnetic coil 104 for limiting axial movement of the coil 104. A second annular plate 110 is arranged at an axial end of the smaller electromagnetic coil 106 for limiting axial movement of the coil 106. The first annular plate 108 is larger than the second annular plate 110. The magnetic core 102, the large electromagnetic coil 104, the small electromagnetic coil 106, the larger annular plate 108, and the smaller annular plate 110 are arranged coaxially.

FIG. 1B shows an electromagnetic device 200 for manipulating a magnetic-responsive robotic device in one embodiment of the invention. The construction of the electromagnetic device 200 in FIG. 1B is similar to the construction of the electromagnetic device 100 in FIG. 1A, except that in FIG. 1B, the annular plates are not shown.

As shown in FIG. 1B, the electromagnetic device 200 includes a magnetic core 202. The magnetic core is an iron core made of DT4E material. DT4E material exhibits good electromagnetic properties, low coercivity, high-saturation magnetic induction, and is less susceptible to magnetic aging problem.

The magnetic core 202 includes a first end and a second end. The magnetic core 202 has a cross section that generally (but not continuously) reduces from the first end to the second end. Specifically, the magnetic core 202 includes a first cylindrical portion 202A and a second cylindrical portion 202B extending from an axial end face of the first cylindrical portion 202A along the same central axis 220. The first cylindrical portion 202A and the second cylindrical portion 202B each have a substantially constant cross sectional area. The cross sectional area of the second cylindrical portion 202B is smaller than that of the first cylindrical portion 202A. The second cylindrical portion 202B forms a stepped portion. The ratio of a diameter of the first cylindrical portion 202A to a diameter of the second cylindrical portion 202B is preferably between 1.1 to 1.5, and more preferably about 1.3. In one example, the diameter of the first cylindrical portion 202A is about 70 mm, the diameter of the second cylindrical portion 202B is about 54 mm, and a length (along the central axis 220) of the first and second portions 202A, 202B combined is about 65 mm.

The magnetic core 200 also includes a third portion 202C extending from an axial end face of the second cylindrical portion 202B along the central axis 220. The third portion 202C is also called the probe portion. The probe portion 202C has a varying cross sectional area. The largest area of the varying cross sectional area is smaller than the cross sectional area of the second cylindrical portion 202B. The probe portion 202C includes a tapering portion 202C2 and a thin cylindrical disk portion 202C1 arranged between the second cylindrical portion 202B and the tapering portion 202C2. The tapering portion 202C2 is a generally conical portion formed by a frustoconical portion that extends from the base and a rounded tip portion at the tip. The rounded tip is in the form of a semi-ellipsoid. The frustoconical portion has a first end and a second end, extending from the base to towards the tip along the central axis 220. In one example, the first end has a diameter of 16 mm to 24 mm and the second end has a diameter of 4 mm to 12 mm. In one preferred embodiment, the first end has a diameter of 20 mm and the second end has a diameter of 8 mm. In another preferred embodiment, the first end has a diameter of 22 mm and the second end has a diameter of 12 mm. The shape and form of the tapering portion 202C2, in particular, the generally conical portion can help increase the divergence of the magnetic induction lines, and consequently, increase the magnetic field gradient.

The magnetic core 200 also includes a fourth cylindrical portion 202D extending from the first cylindrical portion 202A opposite to the second cylindrical portion 202B along the central axis 220. The fourth cylindrical portion 202D has a cross sectional area larger than the cross sectional area of the first cylindrical portion 202A. The fourth cylindrical portion 202D may have a thickness (along the central axis 220) of up to about 9 mm, up to about 7 mm, up to about 5 mm, or up to about 3 mm. The first to fourth portions 202A-202D of the magnetic core 200 are arranged coaxially.

As shown in FIG. 1B, a first electromagnetic coil 204 is arranged around the first cylindrical portion 202A. The first electromagnetic coil 204 preferably includes 300 to 900 turns, 600 to 620 turns, and more preferably has about 610 turns. The first electromagnetic coil 204 is formed by enameled copper wires. The copper wires have a diameter of about 1 mm. A second electromagnetic coil 206 is arranged around the second cylindrical portion 202B. The second electromagnetic coil 206 preferably includes 100 to 300 turns, 180 to 200 turns, and more preferably has about 190 turns. The second electromagnetic coil 206 is formed by enameled copper wires. The copper wires have a diameter of about 1 mm. The first and second electromagnetic coils 204, 206 are generally and the first to fourth portions 202A-202D of the magnetic core 200 are arranged coaxially.

In one embodiment of the invention, the magnetic core 200 design can be optimized based on theoretical analysis: when the magnetic core, e.g., iron core, is in the saturation state, its radius is proportional to the distance from its center point to the concerned position along its normal line in space. This proportional relationship directly affects the magnetic field strength generated by the iron core. The inventors of the present invention has devised, through research, experiments, and trials, that: for the relationship between the radius (R) of the core and the distance (L) from the center point of the iron core to the concerned position (position in which the magnetic field acts) along the normal line of the iron core, when $R=\sqrt{6}/3L$, the maximum magnetic field strength and gradient can be generated by the electromagnetic coil. The shape and size of the iron core can be designed accordingly based on mathematical modeling and parametric optimization using the finite element method. Also, with parametric optimization, the shape and the size of the probe portion and the fourth portion can be determined.

FIG. 1C shows an electromagnetic apparatus 300 formed by four electromagnetic devices 200A-200D of FIG. 1B. As shown in FIG. 1C, the four electromagnetic devices 200A-200D are angularly evenly spaced apart, form two opposite-facing pairs. The probe portions of all four electromagnetic devices 200A-200D points towards a central point in which the robotic device to be manipulated can be placed or arranged.

Figure 1D:
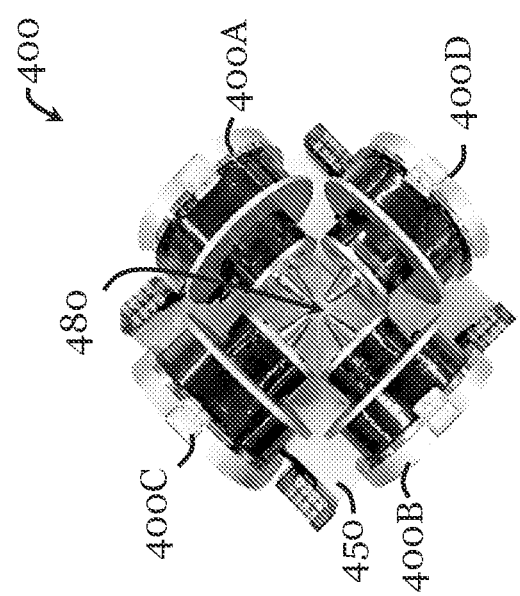
FIG. 1D is a picture of an electromagnetic apparatus fabricated based on FIG. 1C in one embodiment of the invention.

FIG. 1D is an electromagnetic apparatus 400 fabricated based on FIG. 1C. The main difference between the electromagnetic apparatus 400 of FIG. 1D and the electromagnetic devices 300 of FIG. 1C is that the electromagnetic devices 400A-400D of FIG. 1D includes the annular plates such as those illustrated in FIG. 1A. As shown in FIG. 1D, the electromagnetic devices 400A-400D are mounted on a support structure 450 or a mount. A test chamber 480 for receiving the robotic device is arranged at the central point towards which the four electromagnetic devices 400A-400D points.

FIG. 1E is a system 500 incorporating the electromagnetic apparatus 400 of FIG. 1D. The system 500 includes, generally, a power supply 594 and an imaging device. The power supply 594 is a programmable power supply that can provide 500 W power, a stable maximum current of 10 A for a single coil and a total resistance of 5 Ω. The imaging device includes a CCD camera 590, and a microscope 592, arranged above the electromagnetic apparatus 400. In this example, the camera is a THORLABS 1.4-megapixel CCD camera with an imaging area of 8.98 mm×6.71 mm and a pixel size of 6.45 μm×6.45 μm. The frame rate is 1 ms, and the exposure time is 41 fps.

FIGS. 2A to 2F show the optimization of the shape of the magnetic core 200 of the electromagnetic device in some embodiments of the invention and the corresponding simulation results of the magnetic field distribution.

Figure 2A:
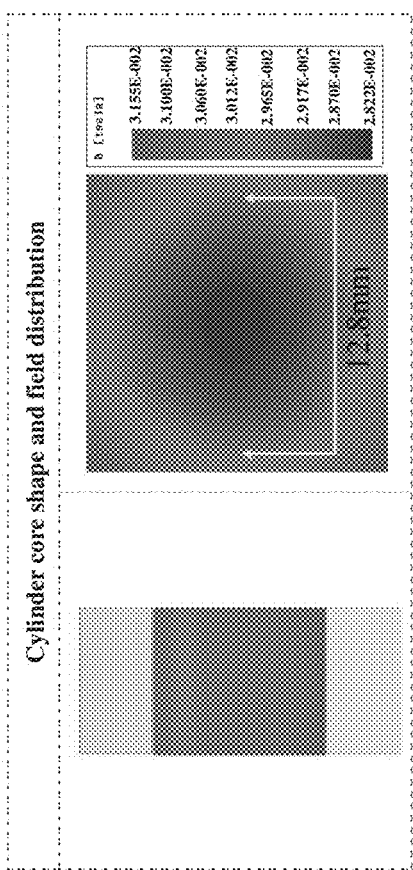
FIG. 2A is a schematic view of an electromagnetic device in one embodiment of the invention, along with a graph showing its simulated magnetic field distribution.

FIG. 2A shows a cylindrical magnetic core 200 structure with a diameter of 65 mm and a length of 60 mm. Under a current of 10 A, the maximum field flux and gradient can reach 27.9 mT and 0.83 T/m, respectively. In this example, the radial dimensions of the front and back of the core have the same core volume considering that the size reduction of the front end of the core may lead to an abrupt release of the concentrated magnetic induction line.

Figure 2B:
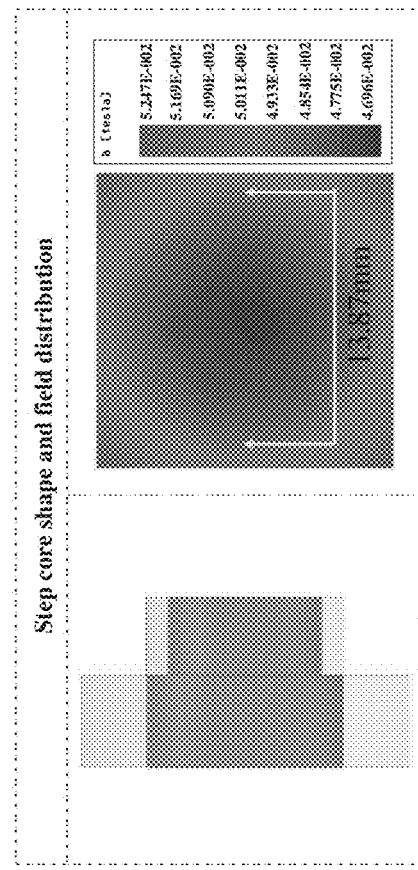
FIG. 2B is a schematic view of an electromagnetic device in one embodiment of the invention, along with a graph showing its simulated magnetic field distribution.

FIG. 2B shows a stepped magnetic core 200 structure with a length (axial) of 65 mm, a larger diameter of 70 mm for the first portion, and a smaller diameter of 54 mm for the second portion. For the same number of turns of coils and the same current as in FIG. 2A, the maximum field flux and gradient of such a stepped magnetic core 200 structure can be increased to 46.5 mT and 1.63 T/m, respectively. The simulation results indicate that the magnetic field gradient increases when the size of the front end of the core is used appropriately.

Figure 2C:
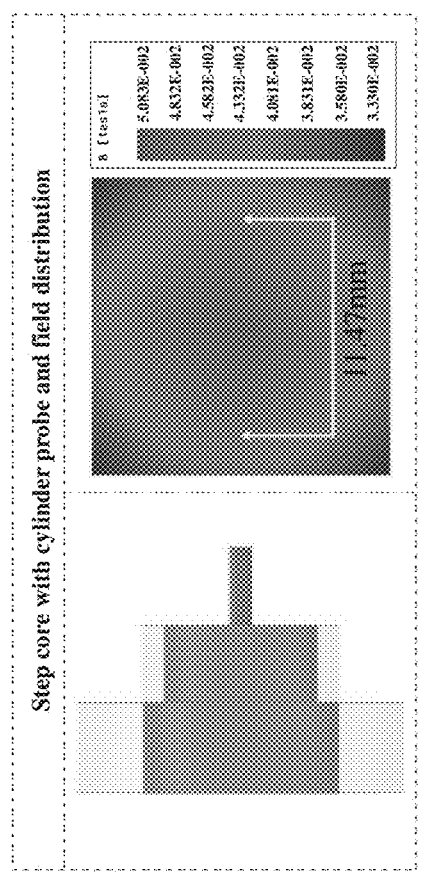
FIG. 2C is a schematic view of an electromagnetic device in one embodiment of the invention, along with a graph showing its simulated magnetic field distribution.

FIG. 2C illustrates a stepped magnetic core 200 structure further including a probe with a small radial dimension added to the front end along the axis. The length and diameter of the probe are 30 mm and 8 mm, respectively. The simulation results show that the maximum field flux and gradient can be further increased to 50.5 mT and 7.95 T/m, respectively.

Figure 2D:
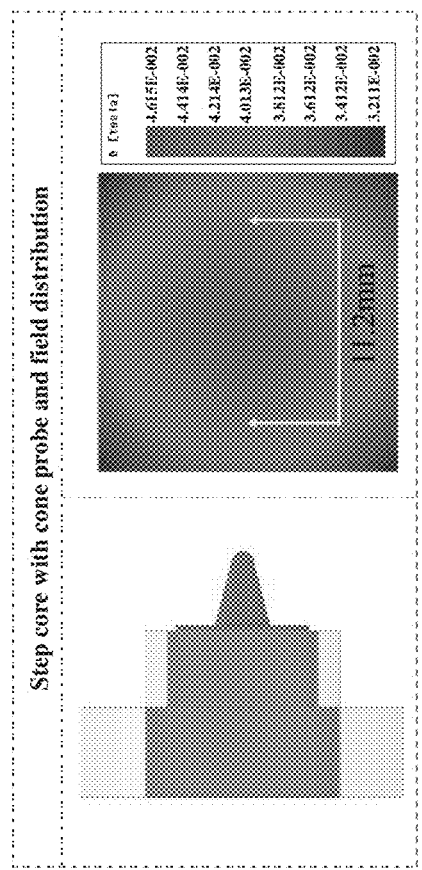
FIG. 2D is a schematic view of an electromagnetic device in one embodiment of the invention, along with a graph showing its simulated magnetic field distribution.
Figure 2E:
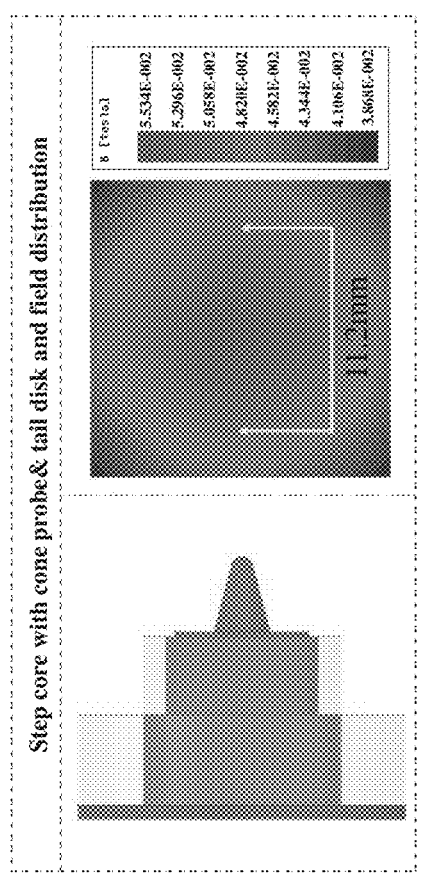
FIG. 2E is a schematic view of an electromagnetic device in one embodiment of the invention, along with a graph showing its simulated magnetic field distribution.

FIGS. 2D and 2E show a stepped magnetic core 200 structure further including a tapering probe structure (FIGS. 2D and 2E) and a thin disk next to the first portion (FIG. 2E). These structures can further increase magnetic field intensity and gradient. In these examples, the use of a probe structure and a thin disk helps reduce the waste produced by the magnetic induction line during transmission and collection after divergence, which has been verified by simulations.

FIG. 2D illustrates a stepped magnetic core 200 structure further including a tapering probe structure and an intermediate thin cylindrical portion between the stepped portion and the probe. In this construction, the maximum magnetic field flux and gradient can reach 46 mT and 9.8 T/m, respectively. The increase in the radial dimension of the probe's root (base, away from the tip) reduces magnetic flux loss in the core.

FIG. 2E shows a stepped magnetic core 200 structure further including a tapering probe structure and an intermediate thin cylindrical portion between the stepped portion and the probe, as well as a further thin disc at the end of the core opposite the probe. In this construction, the maximum magnetic field strength and gradient can be further increased to 55 mT and 12 T/m, respectively.

Figure 2F:
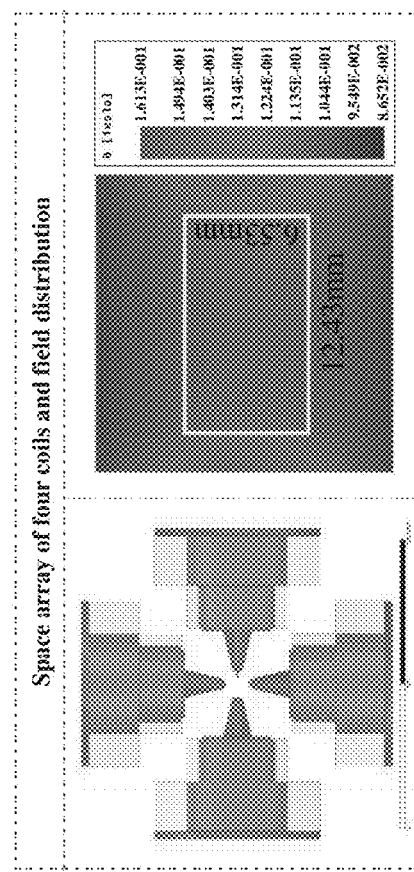
FIG. 2F is a schematic view of an electromagnetic apparatus in one embodiment of the invention, along with a graph showing its simulated magnetic field distribution.
Figure 5A:
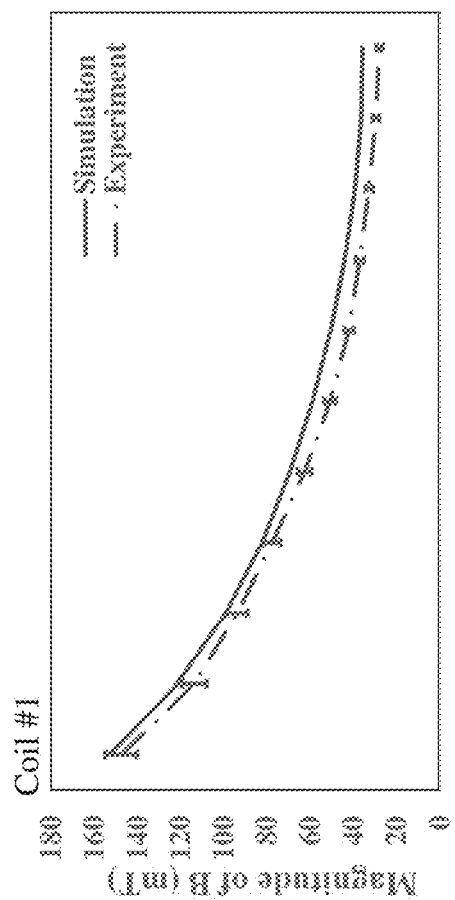
FIG. 5A is a graph showing experimental results of variation of magnetic field intensity (mT) of the first electromagnetic device of the electromagnetic apparatus of FIG. 1D at different positions of the workspace along the core axis when the coil is energized with a current of 5 A, and corresponding simulation results.
Figure 5B:
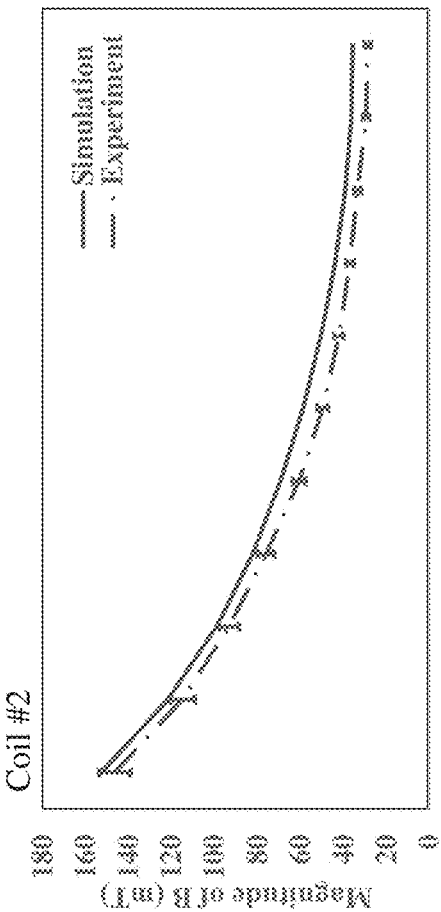
FIG. 5B is a graph showing experimental results of variation of magnetic field intensity (mT) of the second electromagnetic device of the electromagnetic apparatus of FIG. 1D at different positions of the workspace along the core axis when the coil is energized with a current of 5 A, and corresponding simulation results.
Figure 5C:
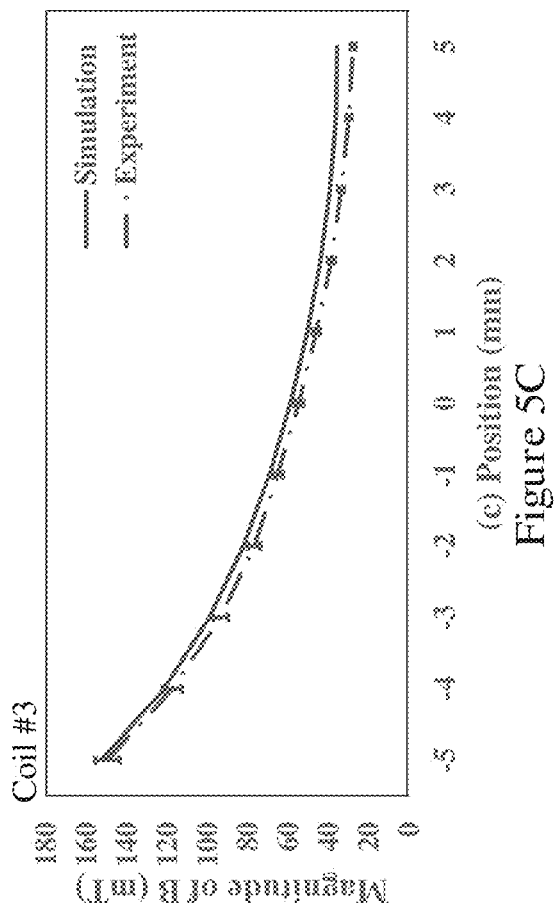
FIG. 5C is a graph showing experimental results of variation of magnetic field intensity (mT) of the third electromagnetic device of the electromagnetic apparatus of FIG. 1D at different positions of the workspace along the core axis when the coil is energized with a current of 5 A, and corresponding simulation results.
Figure 5D:
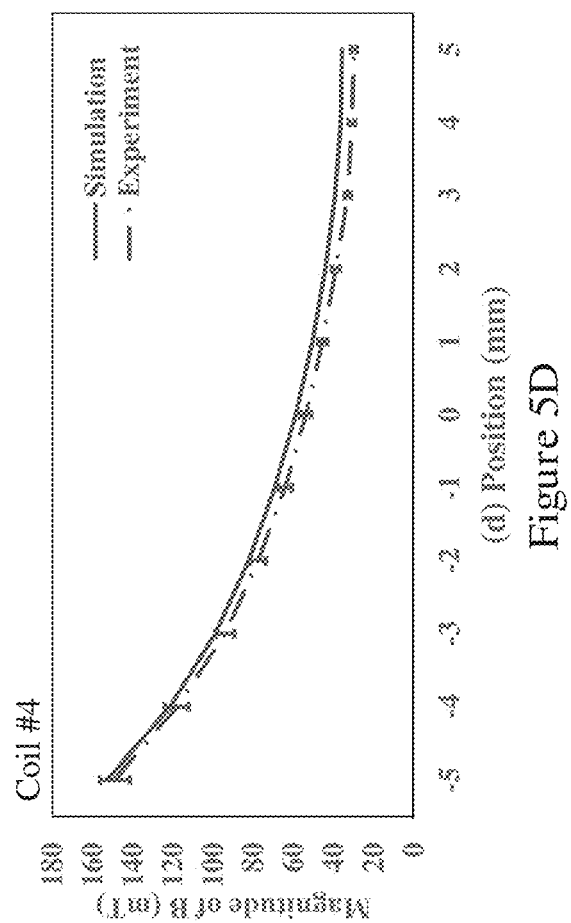
FIG. 5D is a graph showing experimental results of variation of magnetic field intensity (mT) of the fourth electromagnetic device of the electromagnetic apparatus of FIG. 1D at different positions of the workspace along the core axis when the coil is energized with a current of 5 A, and corresponding simulation results.

FIG. 2F illustrates that an electromagnetic apparatus formed by four electromagnetic devices. The array of electromagnetic devices considerably increases the magnetic field strength and gradient. A single electromagnetic device with the optimized iron core can produce a magnetic field strength and gradient of 55 mT and 12 T/m, respectively, with a current input of 10 A when the core axis is 8 mm away. When the four coils are orthogonally distributed as shown (in this example, 16 mm apart), the magnetic field strength and gradient can reach 124.1 mT and 20.1 T/m, respectively.

In the above theoretical analysis, the core material, current, and turn number of coils are the same for a fair comparison. The distance between the core and the center point of the workspace is 8 mm. These examples show that adding the iron core structure to the coils can increase the concentration of the magnetic field. The divergence of the magnetic induction line directly affects the magnitude of the magnetic field gradient. Furthermore, the magnetic field gradient and field fluxes depend on the core shape. The simulation results show that the use of the probe structures can considerably improve the driving ability of the coil and reduce the manipulation space of the coil array.

The effect of the root (base) and dome (tip) diameters of the frustoconical portion of the probe portion of the magnetic core, and the thickness of the disk at the end of the core opposite the tip of the probe portion on the performance of the electromagnetic device of FIG. 1B are examined using a parametric design.

FIGS. 3A and 3B presents the simulation results of the magnetic field intensity and gradient generated by the electromagnetic coils with different probe portions. The diameter of the root (base) range from 16 mm to 24 mm, and the diameter of the dome (tip) ranges from 4 mm to 12 mm, respectively. As shown in FIGS. 3A and 3B, different pairs of dome and root diameters lead to varying magnetic field intensities and gradients. The maximum magnetic field gradient can be obtained when the pairs are (8 mm, 20 mm) and (12 mm, 22 mm). For the generated magnetic field intensity, however, no significant difference exists between the two pairs. Therefore, in one example, the combination of 8 mm and 20 mm is selected as this selection can provide additional space for operations.

FIGS. 3C and 3D presents the simulation results of the magnetic field intensity and gradient generated by the electromagnetic coils with different disk thicknesses (the disk at the end of the core opposite the tip of the probe portion). As shown in FIGS. 3C and 3D, the disk can enhance magnetic field intensity and gradient. However, further increasing disk thickness beyond 3 mm cannot evidently change magnetic field performance. Based on the above theoretical analysis, the core shape in FIG. 1B was thus selected for fabrication of the prototype of FIG. 1D.

The performance of the developed electromagnetic device and apparatus, with the core shape design illustrated, is evaluated based on the magnetic field magnitude and gradient at the central area of the workspace (at the center to which the probe portion of the electromagnetic devices points). The field magnitude reflects the magnetization of the magnetic material used in (e.g., coated on) the microrobot. Stronger magnetization indicates a stronger magnetic force applied to the microrobot. The magnetic field gradient reflects the force acting on the microrobot. A more powerful force can make the operation of the microrobots more effective in complex in vivo environments. The inventors of the present invention has devised, through research, experiments, and trials, that: the material tends to become saturated when the external magnetic field is approximately 150 mT and reaches magnetic saturation when field magnitude is approximately 600 mT. Also, further increasing the external field magnitude will not enhance saturation.

FIGS. 4A and 4B show the simulated variation of the magnetic field and magnetic field intensity produced by the electromagnetic apparatus of FIG. 1C at the center of the workspace under different coil energization currents. As illustrated in FIG. 4A, the magnetic field intensity at the center of the workspace can reach the maximum value of 139.2 mT when the single coil is energized with 10 A. Given such field magnitude, the magnetic material is nearly saturated. Thus, the system is capable of magnetizing and substantially saturating the magnetic material coated on the microrobot. A high magnetic field gradient indicates a strong actuation capability of the electromagnetic manipulation system.

The inventors of the present invention has devised, through research, experiments, and trials, that: for most existing systems, the maximum magnetic field gradient at the center of the workspace can reach nearly 5 T/m. The magnetic field gradient of the system (apparatus, device) in the above embodiments tends to change linearly with the current when the optimized coil number and core shape are used. As shown in FIG. 4B, when the conduction current is 10 A, the magnetic field gradient at the center of the workspace can reach a maximum of 20.15 T/m. Such magnetic field gradient considerably enhances the driving capacity of the microrobot and enables its effective actuation in in vivo environments.

FIGS. 5A to 5D illustrate the magnetic field intensity at the center of the workspace, with the simulation and experimental results of magnitude B at different positions of the workspace along the core axis of the respective electromagnetic devices when the corresponding coil is energized with a current of 5 A. As shown in FIGS. 5A to 5D, the simulation results exhibit good agreement with the experimental results, which verifies the accuracy of the theoretical design.

Experiments were performed using the system of FIG. 1E (and the apparatus of FIG. 1D) to determine the performance of the apparatus.

Figure 6A:
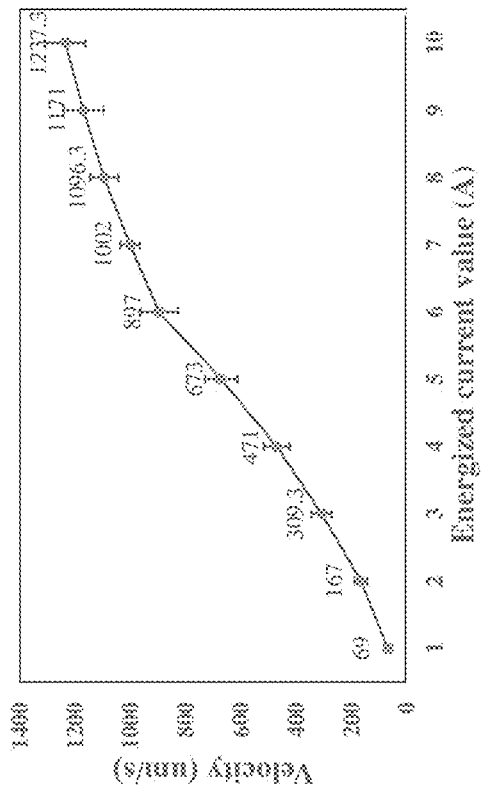
FIG. 6A is a graph showing experimental results of variation of movement velocity (m/s) of a microrobot immersed in pure water and manipulated by the electromagnetic apparatus of FIG. 1D, and the current (A) applied to the coil of the electromagnetic apparatus of FIG. 1D.
Figure 6B:
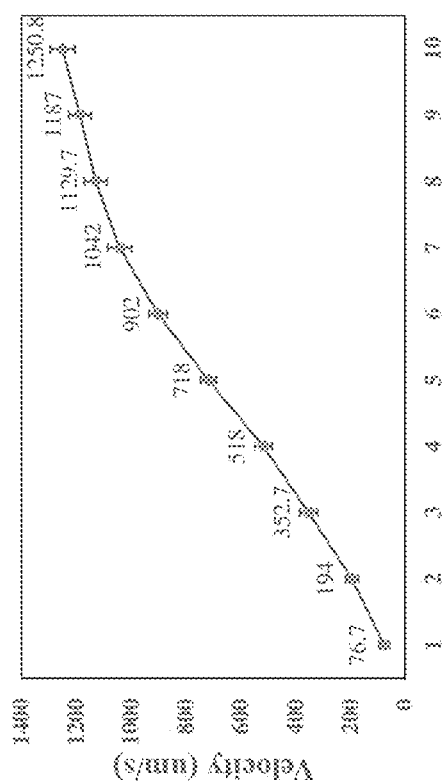
FIG. 6B is a graph showing experimental results of variation of movement velocity (m/s) of a microrobot immersed in artificial cerebrospinal fluid and manipulated by the electromagnetic apparatus of FIG. 1D, and the current (A) applied to the coil of the electromagnetic apparatus of FIG. 1D.
Figure 6C:
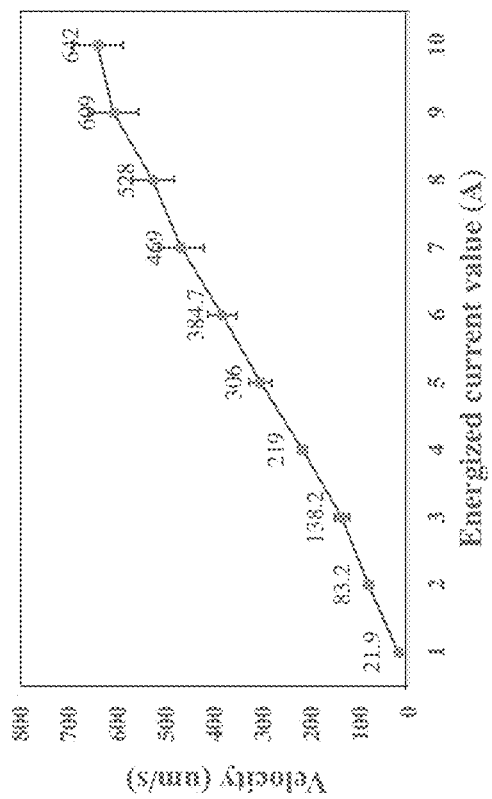
FIG. 6C is a graph showing experimental results of variation of movement velocity (m/s) of a microrobot immersed in mouse blood and manipulated by the electromagnetic apparatus of FIG. 1D, and the current (A) applied to the coil of the electromagnetic apparatus of FIG. 1D.
Figure 6D:
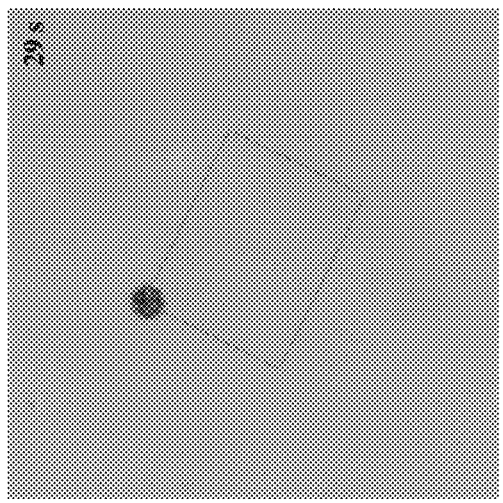
FIG. 6D is a picture showing a location of the microrobot immersed in a liquid environment having a viscosity of 300 mPa·s and manipulated by the electromagnetic apparatus of FIG. 1D at a first instant (29 s)
Figure 6E:
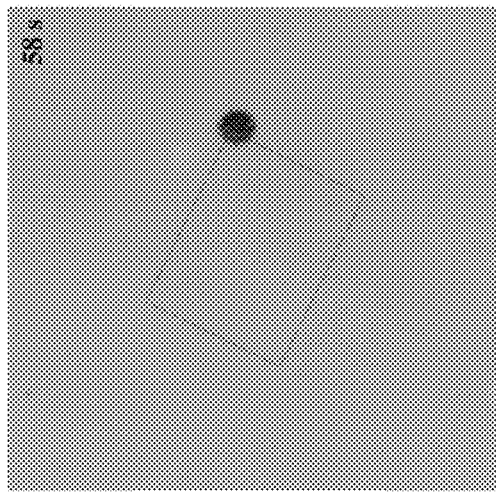
FIG. 6E is a picture showing a location of the microrobot immersed in a liquid environment having a viscosity of 300 mPa·s and manipulated by the electromagnetic apparatus of FIG. 1D at a second instant (58 s)
Figure 6F:
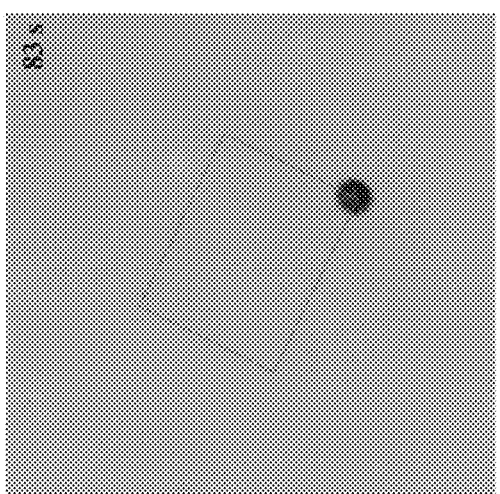
FIG. 6F is a picture showing a location of the microrobot immersed in a liquid environment having a viscosity of 300 mPa·s and manipulated by the electromagnetic apparatus of FIG. 1D at a third instant (83 s)
Figure 6G:
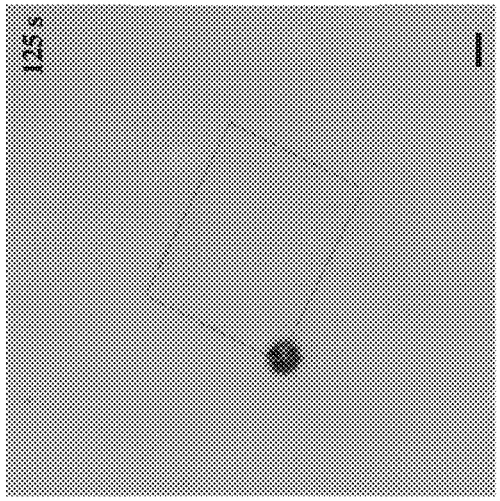
FIG. 6G is a picture showing a location of the microrobot immersed in a liquid environment having a viscosity of 300 mPa·s and manipulated by the electromagnetic apparatus of FIG. 1D at a fourth instant (125 s)

FIGS. 6A to 6C show experimental results of variation of movement velocity of a microrobot immersed in different liquids (different viscosities) and manipulated by the electromagnetic apparatus of FIG. 1D, and the current applied to the coil of the electromagnetic apparatus of FIG. 1D.

FIG. 6A shows the results when pure water of 1 mPa·s is used as the liquid in which the microrobot immerses. In this experiment, the accuracy of the alignment of the electromagnetic coil was compensated. A graph that depicts the relationship between the velocity of the microrobot and the current is illustrated in FIG. 6A. As shown in the figure, the microrobot had a velocity of 76.7±15 μm/s when the current was 1 A, thereby showing that the system can effectively control the microrobot starting from a current of 1 A. When the current was 10 A, the microrobot reached a maximum velocity of 1250.8±44 μm/s.

FIG. 6B shows the results of the second test, when artificial cerebrospinal fluid is used as the liquid in which the microrobot immerses. In in vivo environment, liquids, such as cerebrospinal and synovial fluids, are typically static. When problems occur, such as bleeding and wear in the cranial and joint cavities, respectively, conducting surgery in this small space using the traditional method is difficult. The use of microrobots can help solve this problem. Given that artificial and real cerebrospinal fluids have nearly the same contents, the data obtained from the actuation experiment in the artificial cerebrospinal fluid can have high relevance in real applications. FIG. 6B illustrates the relationship between the input current and the velocity of the microrobot in the artificial cerebrospinal fluid test. Given the current of 1 A, the velocity of the microrobot can reach 69±13 μm/s. This result indicates that the platform can effectively actuate the microrobot in liquids with higher viscosity than pure water. When the current was 10 A, the velocity of the microrobot reached the maximum value of 1237.3±73 μm/s.

FIG. 6C shows the results of the second test, when mouse blood is used as the liquid in which the microrobot immerses. Blood is an uneven fluid that contains red and white blood cells and platelets. The viscosity of blood is 4 mPa·s, which is approximately 4 times that of pure water. In one example the blood flow rate of an adult is 18-22 cm/s in the aorta, 7-8 cm/s in the vena cava, and 0.3-0.7 mm/s in the capillary. In an environment with high fluid speed, the effective operation of microrobots is challenging. With the system and apparatus of the above embodiment, the microrobots were driven and controlled in mouse blood, and the relationship between the current value and the motion velocity of the microrobot was obtained, as shown in FIG. 6C. As indicated in the figure, the microrobot can reach a speed of 642±53 μm/s. The motion resistance of the microrobot in the blood mainly depends on its speed in relation to the fluid. The result in FIG. 6C indicates an effective capability of the developed system in driving microrobots.

FIGS. 6D to 6G show pictures indicating location of the microrobot immersed in a liquid environment having a viscosity of 300 mPa·s and manipulated by the electromagnetic apparatus of FIG. 1D. This in vitro experiment was performed in a special fluid environment with an extremely high viscosity to further prove the powerful driving ability of the system and apparatus of the present embodiment. When a current of 10 A is used, the microrobot was actuated by the electromagnetic devices in a liquid with a viscosity that was 300 times that of pure water. The microrobot traveled in a rectangular path in the liquid environment and eventually returned to the starting point. As driving the microrobot with a low current is a challenge due to high resistance of the liquid, the experiments were performed with a maximum current of 10 A.

Figure 7B:
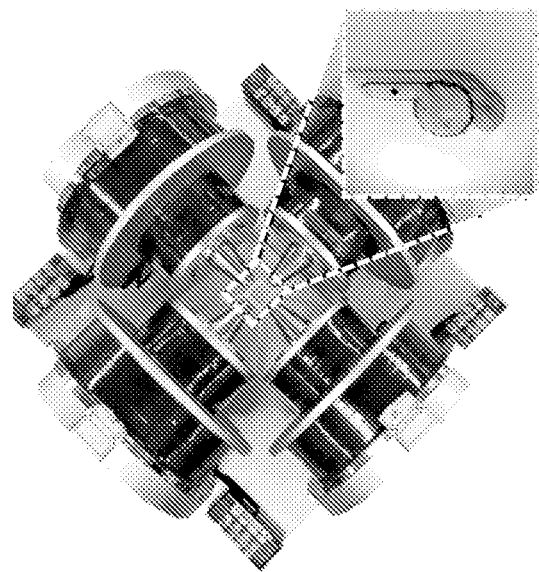
FIG. 7B is a picture showing the setup of the electromagnetic apparatus of FIG. 1D to manipulate the microrobot in the zebrafish yolk.
Figure 7A:
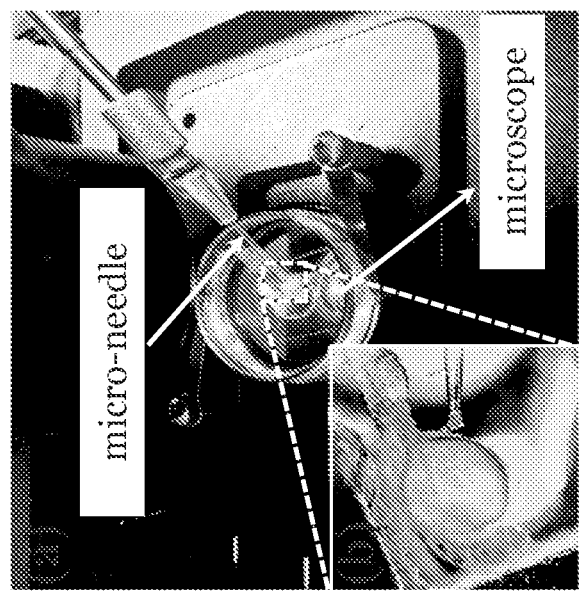
FIG. 7A is a picture showing injection of a microrobot into zebrafish yolk using the micro-injection system in one example for testing the electromagnetic apparatus of FIG. 1D, with an enlarged view of the microrobot being jammed at the tip of the microneedle with 50 μm opening.
Figure 7C:
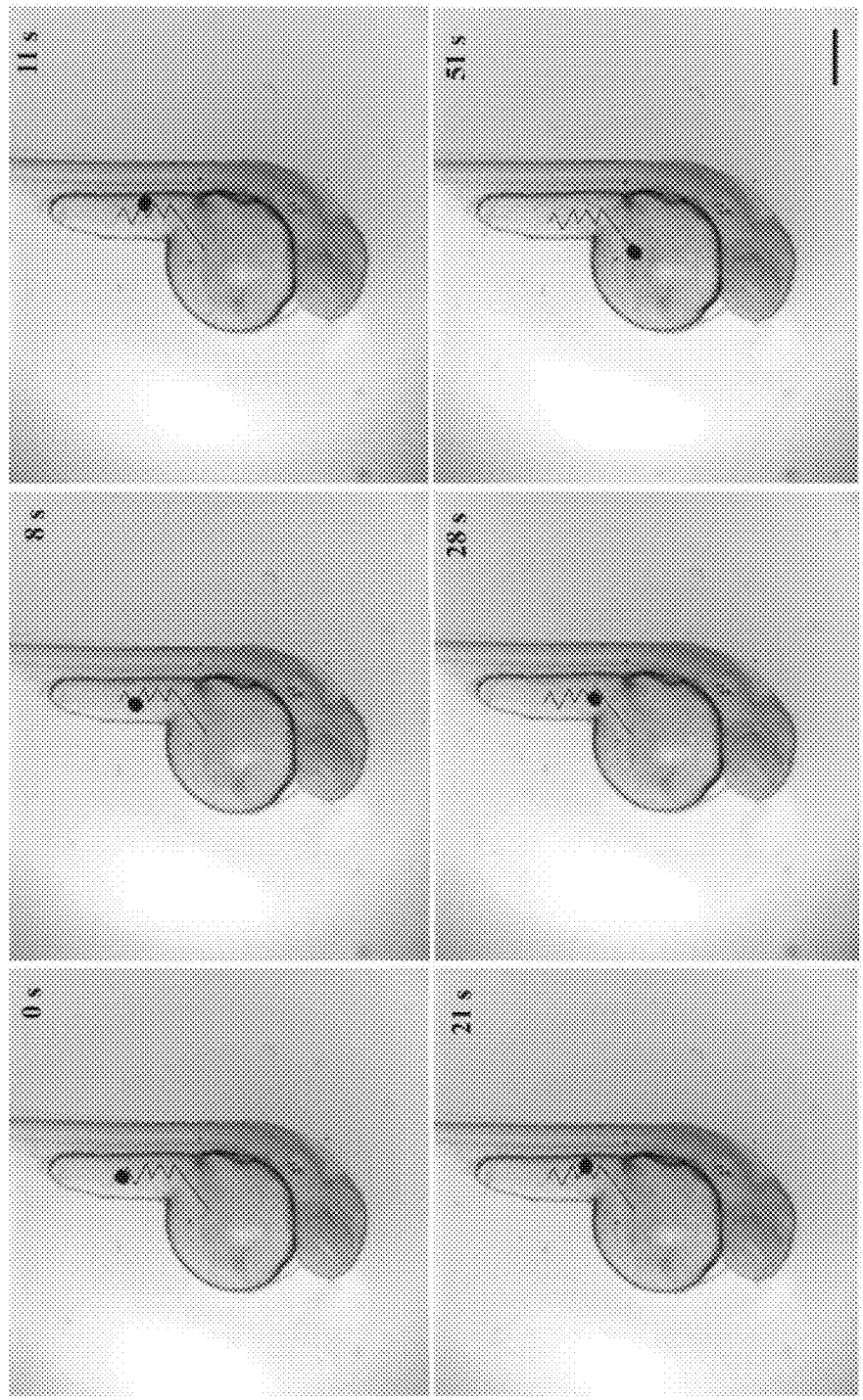
FIG. 7C is a series of pictures showing movement of the microrobot in the zebrafish yolk when the microrobot is under the control of the electromagnetic apparatus of FIG. 1D.

In vivo experiments were also performed in zebrafish yolk. The inventors of the present invention has devised, through research, experiments, and trials, that: zebrafish exhibits high similarity to humans, and postnatal zebrafish yolk remains transparent, which considerably simplifies the in vivo imaging process. During the experiments, as shown in FIGS. 7A and 7B, a microinjection system was used to insert the microrobots into zebrafish yolk. The tip of the microinjection needle measured 40-50 μm. The anesthetized zebrafish was placed on a small dish to conduct microinjection. A negative pressure was applied to the needle tip by a hydraulic pump connected to the needle terminal catheter to fix the microrobot. The microrobot was successfully driven by the electromagnetic apparatus, as shown in FIG. 7C. The microrobot moved from the elongated to rounded portion of the yolk with a total time of 51 s, as indicated in FIG. 7C. The zebrafish yolk is filled with dense and unevenly distributed materials. Such a complex environment posed difficultly in actuating and controlling the microrobot. The microrobot moved from the elongated to the rounded portion of the yolk by moving along the "Z" path to overcome the resistance from the materials.

Figure 8:
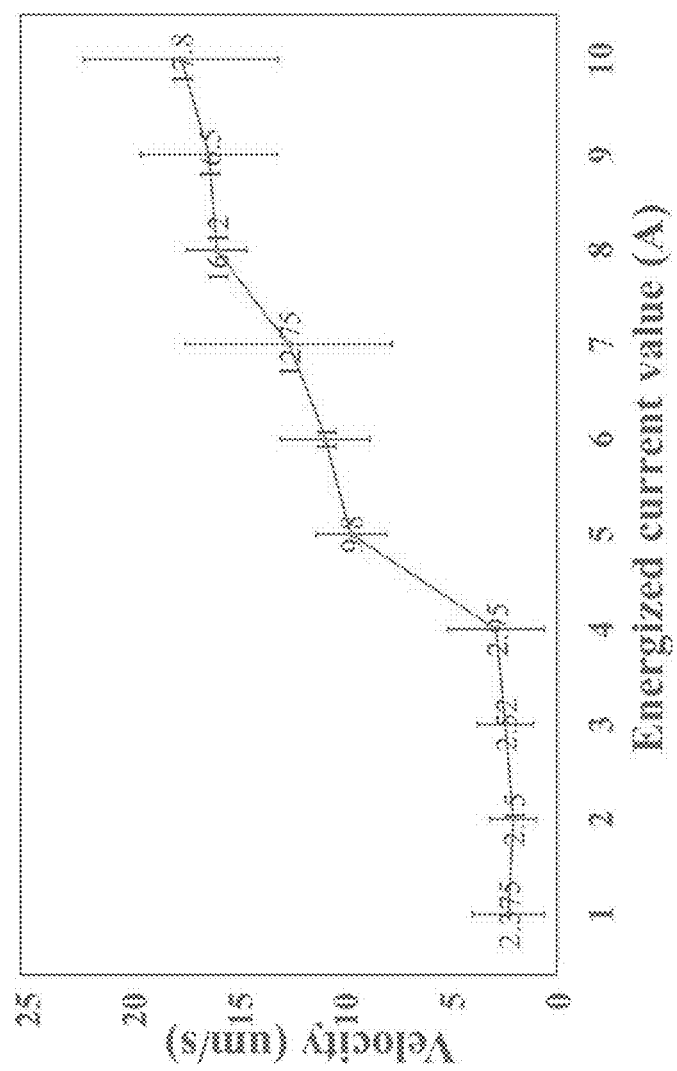
FIG. 8 is a plot showing variation between the movement velocity of the microrobot in the zebrafish yolk and the current supplied to the electromagnetic apparatus of FIG. 1D.
Figure 9:
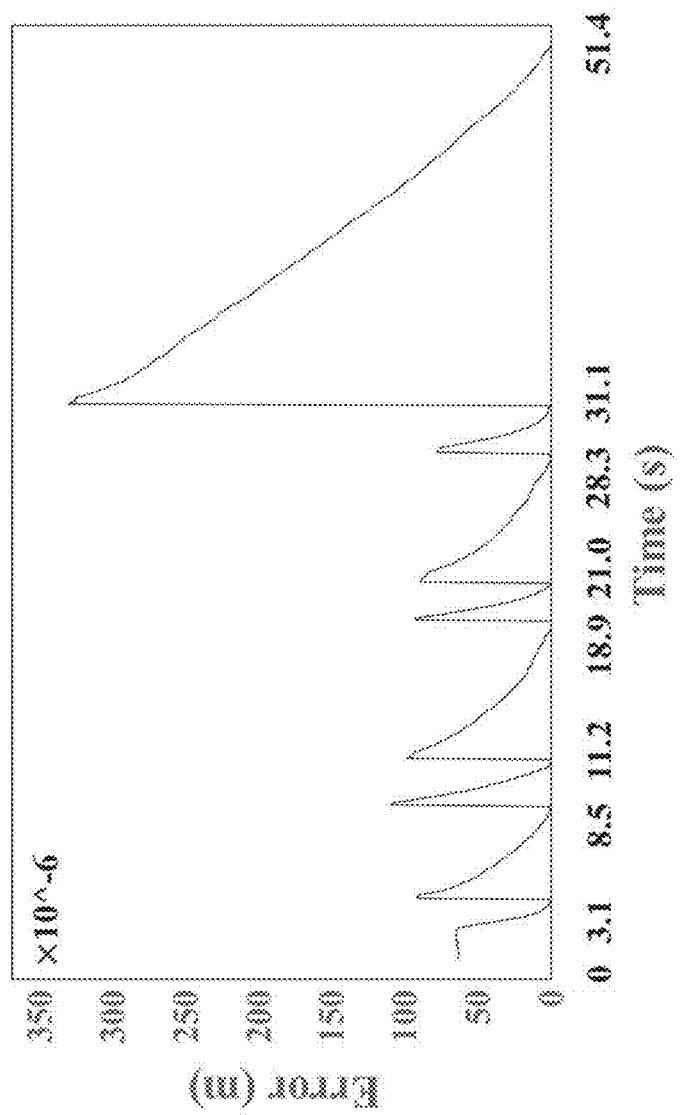
FIG. 9 is a plot showing the measured positional error of the microrobot in the zebrafish yolk when the microrobot is under the control of the electromagnetic apparatus of FIG. 1D.

FIG. 8 shows the measured velocity of the microrobot, in particular the relationship between the velocity of the microrobot and the coil current. FIG. 9 shows the position error of the microrobot calculated using MATLAB. During the experiment, eight points were marked by the operator, and the microrobot moved from the starting point to the end point through the path connected by the eight target points. The experimental results show that the developed magnetic platform is effective in actuating and controlling the microrobot in an in vivo environment.

The performance of the electromagnetic apparatus of the above embodiment is compared with those of some existing like electromagnetic apparatuses. These existing apparatuses include disclosed those in:

- M. P. Kummer, J. J. Abbott, B. E. Kratochvil, R. Borer, A. Sengul, and B. J. Nelson, "*OctoMag: An electromagnetic system for 5-DOF wireless micromanipulation,*" *IEEE Transactions on Robotics,* vol. 26, pp. 1006-1017, 2010 ("Octomag" in FIG. 10)
- F. Niu, J. Li, W. Ma, J. Yang, and D. Sun, "*Development of an Enhanced Electromagnetic Actuation System with Enlarged Workspace,*" *IEEE/ASME Transactions on Mechatronics,* vol. 22, pp. 2265-2276, 2017 ("System A" in FIG. 10)
- E. Diller, J. Giltinan, G. Z. Lum, Z. Ye, and M. Sitti, "*Six-degree-of-freedom magnetic actuation for wireless microrobotics,*" *The International Journal of Robotics Research,* vol. 35, pp. 114-128, 2016 ("MaguBot" in FIG. 10)

Figure 10:
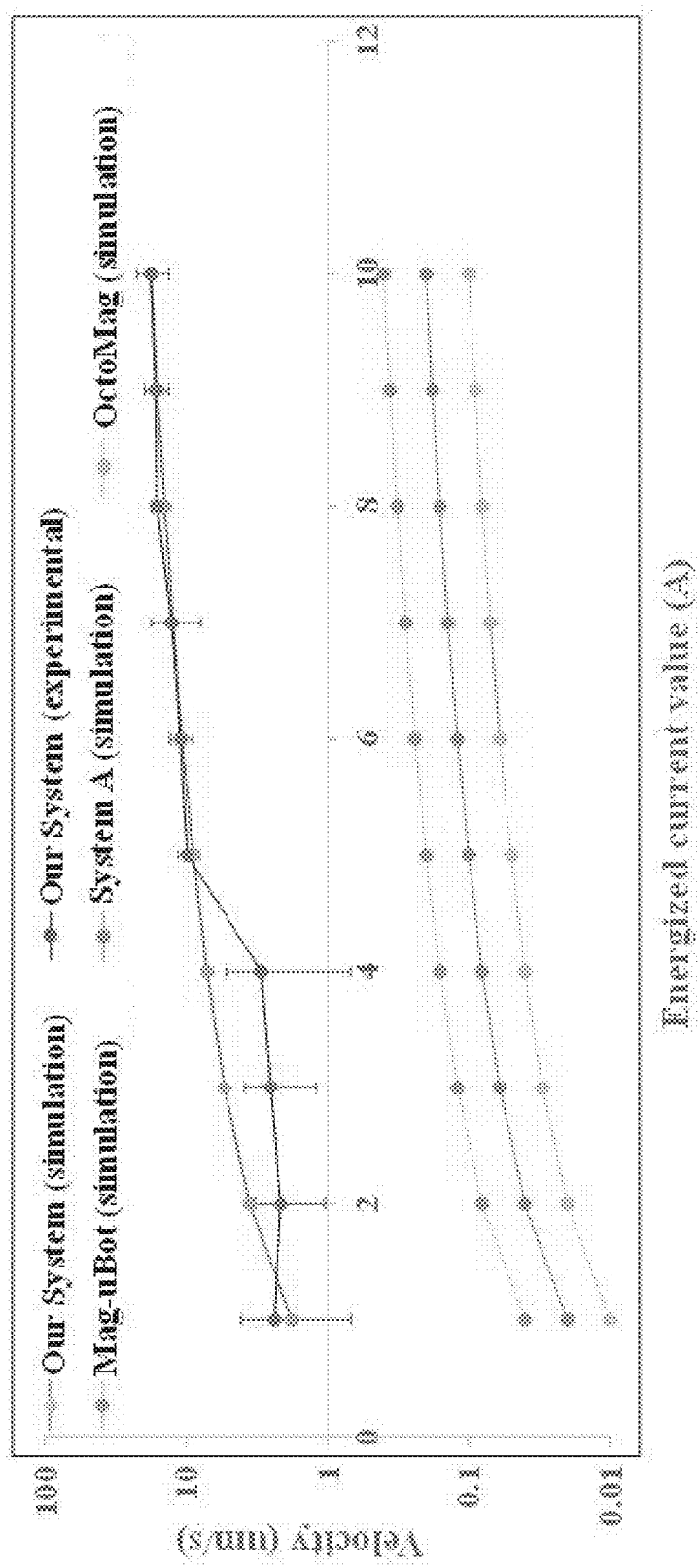
FIG. 10 is a graph showing comparison of performance of the electromagnetic apparatus of FIG. 1D with some existing electromagnetic apparatuses.

Based on the system parameters reported in the above references, the relationships between the velocity of the microrobot and the coil current under several electromagnetic manipulation systems are shown in FIG. 10. As illustrated in FIG. 10, the velocity of the microrobot under the actuation of the electromagnetic apparatus of the above embodiment can reach more than 10 µm/s. This indicates that the electromagnetic apparatus of the above embodiment can effectively manipulate the microrobot in zebrafish yolk. Under the actuations of three other existing systems, the velocities of the microrobot are all less than 1 µm/s. This indicates that the microrobot is barely driven in the in vivo environment of zebrafish yolk using these known systems.

The above embodiments of the invention have provided an electromagnetic device and related apparatus with a characteristic magnetic core 200 design. he above embodiments of the invention have provided a magnetic gradient field-based actuation system that can enable effective manipulation of magnetic-responsive robotic devices, such as microrobotic devices that are often employed in harsh environments. The shape and size of the iron core are designed based on mathematical modeling and parametric optimization using the finite element method. Through the characteristic core shape design, the magnetic field generated by the electromagnetic actuation system of the above embodiments can be considerably enhanced to propel microrobots in in-vivo environments. The above embodiments provide gradient enhancement of electromagnetic actuation. Compared with some existing systems, the system, apparatus and device in the above embodiments can generate a considerably higher magnetic field flux and gradient of 115.5 mT and 20 T/m, respectively, which render the in vivo and in vitro actuation of microrobots feasible and efficient. The embodiments of the invention provides better robotic device driving capability, especially when the apparatus or device is used in gradient magnetic field driving mode. The use of magnet and magnetization is non-invasive and hence suitable for biomedical applications. Also, with the enhanced magnetic field and gradient, specific design requirement on the robotic device (e.g., how the magnet is arranged, how much magnetic material should be used, etc.) can be relaxed. In one application, the apparatus and device can be used to actuate the microrobots carrying of drugs or cells to achieve minimally invasive surgery with high precision.

It will be appreciated by persons skilled in the art that numerous variations and/or modifications may be made to the invention as shown in the specific embodiments without departing from the spirit or scope of the invention as broadly described. The described embodiments of the invention should therefore be considered in all respects as illustrative, not restrictive. For example, the shape and/or form of the magnetic core 200 can vary, with additional parts, reduced parts, or parts having a different shape and form from those described. Preferably, the magnetic core 200 has a generally tapering form from one end to the other. The material of the magnetic core 200 need not be DT4E, but can be any other materials suited for a magnetic core. The dimension and dimension ratio of the magnetic core 200 parts can be scaled or different from those described. The numbers of electromagnetic coils and the number of turns of each coil can be different from those described. The materials of the wires can be different. The axial alignment of the different parts of the electromagnetic device can be modified, offset, etc. The electromagnetic apparatus can have a different number of electromagnetic devices, arranged in a different geometry, and/or on a mount with a different shape/form.

The invention claimed is:

1. An electromagnetic device for manipulating a magnetic-responsive robotic device, comprising:
    a magnetic core having
        a first portion having a first cross section and defining a first central axis;
        a second portion extending from one side of the first portion, the second portion having a second cross section smaller than the first cross section, and defining a second central axis parallel to the first central axis; and
        a third portion extending from one side of the second portion opposite the first portion, and defining a third central axis parallel to the first and second central axes; and
    one or more electromagnetic coils arranged around the magnetic core;
    wherein the third portion comprises a generally conical portion that tapers away from the second portion and includes a base and a tip, and
    wherein the generally conical portion is formed by a frustoconical portion that extends from the base and a rounded tip portion at the tip.

2. The electromagnetic device of claim 1, wherein the one or more electromagnetic coils comprises a first electromagnetic coil arranged around the first portion and a second electromagnetic coil arranged around the second portion.

3. The electromagnetic device of claim 1, wherein the second portion forms a stepped portion.

4. The electromagnetic device of claim 1, wherein the first central axis and second central axes are collinear.

5. The electromagnetic device of claim 1, wherein the first cross section has a first shape, the second cross section has a second shape, and the first shape is the same as the second shape.

6. The electromagnetic device of claim 1, wherein the first portion is cylindrical and/or the second portion is cylindrical.

7. The electromagnetic device of claim 1, wherein the first portion and the second portion are both cylindrical; and a ratio of a diameter of the first portion to a diameter of the second portion is between 1.1 to 1.5.

8. The electromagnetic device of claim 1, wherein the first, second, and third central axes are collinear.

9. The electromagnetic device of claim 1, wherein the third portion further comprises a thin intermediate portion arranged between the second portion and the generally conical portion, wherein a cross section of the thin intermediate portion is smaller than the second cross section of the second portion.

10. The electromagnetic device of claim 9, wherein the thin intermediate portion is cylindrical.

11. The electromagnetic device of claim 1, wherein the magnetic core further comprises:
    a fourth portion extending from the first portion opposite to the second portion, the fourth portion having a fourth cross section larger than the first cross section, and defining a fourth central axis parallel to the first and second central axes.

12. The electromagnetic device of claim 11, wherein the first, second, and fourth central axes are collinear.

13. The electromagnetic device of claim 12, wherein the first cross section has a first shape, the fourth cross section with a fourth shape, and the first shape is the same as the fourth shape.

14. The electromagnetic device of claim 13, wherein the fourth portion is cylindrical.

15. The electromagnetic device of claim 1, wherein the magnetic core is an iron core made of DT4E material.

16. An electromagnetic device for manipulating a magnetic-responsive robotic device, comprising:

a magnetic core having a first end and a second end, the magnetic core having a cross section that generally reduces from the first end to the second end; and one or more electromagnetic coils arranged around the magnetic core;

wherein the magnetic core comprises:
- a first portion with a first cross section and defining a first central axis;
- a second portion extending from one side of the first portion, the second portion having a second cross section smaller than the first cross section and defining a second central axis parallel to the first central axis;
- a third portion extending from one side of the second portion opposite the first portion, the third portion having a third cross section smaller than the second cross section and defining a third central axis parallel to the first and second central axes; and
- wherein the third portion comprises a generally conical portion that tapers away from the second portion and includes a base and a tip, and
- wherein the generally conical portion is formed by a frustoconical portion that extends from the base and a rounded tip portion at the tip.

17. The electromagnetic device of claim 16, wherein the magnetic core further comprises:
- a fourth portion extending from the first portion opposite to the second portion, the fourth portion having a fourth cross section larger than the first cross section and defining a fourth central axis parallel to the first and second central axes.

18. The electromagnetic device of claim 17, wherein the second portion is a stepped portion.

19. The electromagnetic device of claim 17, wherein the first, second, third, and fourth central axes are collinear.

20. The electromagnetic device of claim 17, wherein the first cross section has a first shape, the second cross section has a second shape, the third cross section has a third shape, and the fourth portion has a fourth shape;
wherein the first, second, third, and fourth shapes are the same.

21. The electromagnetic device of claim 17, wherein the one or more electromagnetic coils comprises:
- a first electromagnetic coil arranged around the first portion; and
- a second electromagnetic coil arranged around the second portion.

22. The electromagnetic device of claim 17, wherein the first, second, and fourth portions are cylindrical.

23. The electromagnetic device of claim 16, wherein the third portion further comprises a thin intermediate portion arranged between the second portion and the generally conical portion, wherein the thin intermediate portion is cylindrical, and wherein a cross section of the thin intermediate portion is smaller than a cross section of the second portion.

24. An electromagnetic apparatus for manipulating a magnetic-responsive robotic device, comprising:
- a plurality of electromagnetic devices of claim 16; and
- a mount for mounting the plurality of electromagnetic devices.

25. The electromagnetic apparatus of claim 24, wherein the plurality of electromagnetic devices are angularly spaced apart evenly.

26. The electromagnetic apparatus of claim 24, wherein the plurality of electromagnetic devices includes four electromagnetic devices.

27. The electromagnetic apparatus of claim 24, wherein the mount supports the plurality of electromagnetic devices such that the plurality of electromagnetic devices generally lies on the same plane.

28. The electromagnetic apparatus of claim 24, further comprising one or more of:
- a power supply operably connected with the plurality of electromagnetic devices for selectively energizing the plurality of electromagnetic devices; and
- an imaging device, arranged to be operably connected with the power supply, for imaging the magnetic-responsive robotic device when the magnetic-responsive robotic device is manipulated by the electromagnetic apparatus.

29. The electromagnetic apparatus of claim 24, wherein the magnetic-responsive robotic device includes one or more magnetic-responsive materials and the electromagnetic apparatus is arranged to saturate the one or more magnetic-responsive materials of the magnetic-responsive robotic device.

30. The electromagnetic device of claim 1, where the rounded tip is in the form of a semi-ellipsoid.

31. The electromagnetic device of claim 16, where the rounded tip is in the form of a semi-ellipsoid.

* * * * *